(12) United States Patent
Miller

(10) Patent No.: US 10,551,287 B2
(45) Date of Patent: Feb. 4, 2020

(54) LARGE SAMPLE TESTING DEVICE, METHOD, AND SYSTEM

(71) Applicant: Stress Engineering Services, Inc., Houston, TX (US)

(72) Inventor: Jack Miller, Houston, TX (US)

(73) Assignee: Stress Engineering Services, Inc., Houston, TX (US)

( * ) Notice: Subject to any disclaimer, the term of this patent is extended or adjusted under 35 U.S.C. 154(b) by 240 days.

(21) Appl. No.: 15/558,054

(22) PCT Filed: Mar. 11, 2016

(86) PCT No.: PCT/US2016/022171
§ 371 (c)(1),
(2) Date: Sep. 13, 2017

(87) PCT Pub. No.: WO2016/149135
PCT Pub. Date: Sep. 22, 2016

(65) Prior Publication Data
US 2018/0067027 A1    Mar. 8, 2018

Related U.S. Application Data

(60) Provisional application No. 62/132,935, filed on Mar. 13, 2015.

(51) Int. Cl.
*G01N 3/10* (2006.01)
*G01N 3/02* (2006.01)
*G01N 3/20* (2006.01)

(52) U.S. Cl.
CPC ............... *G01N 3/10* (2013.01); *G01N 3/02* (2013.01); *G01N 3/20* (2013.01); *G01N 2203/0435* (2013.01)

(58) Field of Classification Search
CPC .. G01N 3/10; G01N 3/02; G01N 3/20; G01N 2203/0435
USPC ............................................. 73/798
See application file for complete search history.

(56) References Cited

U.S. PATENT DOCUMENTS

| | | | |
|---|---|---|---|
| 5,507,339 A | 4/1996 | Holbrook | |
| 5,959,215 A * | 9/1999 | Ono ................. | G01N 3/36 73/789 |
| 7,591,190 B2 * | 9/2009 | Asher ............... | B66D 3/14 73/856 |
| 2003/0192385 A1 * | 10/2003 | Uhlik ................ | G01N 3/20 73/852 |
| 2013/0125661 A1 * | 5/2013 | Arzoumanidis ... | G01B 5/30 73/781 |
| 2013/0247680 A1 | 9/2013 | Ota | |

(Continued)

OTHER PUBLICATIONS

Notification of Transmittal of the International Search Report and the Written Opinion of the International Searching Authority, or the declaration, PCT Application No. PCT/US2016/22171, dated May 23, 2016; 11 pages.

(Continued)

*Primary Examiner* — Jamel E Williams
(74) *Attorney, Agent, or Firm* — Christopher McKeon; Arnold & Saunders, LLP

(57) ABSTRACT

The present invention includes a load frame test device using a plurality of levers about a common pivot point for applying combinations of tensile loading and bending on test articles at magnitudes seen in offshore applications.

31 Claims, 7 Drawing Sheets

(56) References Cited

U.S. PATENT DOCUMENTS

2015/0338325 A1* 11/2015 Kismarton ............... G01N 3/02
73/788
2017/0138827 A1* 5/2017 Mourad ................... G01N 3/02

OTHER PUBLICATIONS

Notification Concerning Transmittal of International Preliminary Report on Patentability based on PCT Application No. PCT/US2016/22171, dated Sep. 28, 2017, 9 pages.

* cited by examiner

LARGE SAMPLE TESTING DEVICE, METHOD, AND SYSTEM

RELATED APPLICATIONS

This application claims priority to U.S. Provisional Application No. 62/132,935, filed Mar. 13, 2015.

BACKGROUND OF THE INVENTION

Subsea hydrocarbon exploration and production presents enormous challenges to operators. The combination of high temperature and high pressures that oilfield equipment has to withstand requires a high degree of testing and qualification. Drilling and production equipment, including casing, wellheads, risers, connections, and other associated equipment must be designed to sustain high load conditions. These conditions are compounded by the fact that offshore oilfield operations are not on a stable platform compared to a land-based oilfield operation. For instance, the wave induced motion of an offshore deepwater rig causes bending moments in the tubing that would not otherwise occur on a stationary land rig. As a result, these stresses and bending moments must be considered when designing and testing tubulars for offshore operations.

Tubulars used offshore experience higher than normal loads in terms of magnitude and non-normal orientations. For instance, when a tubular is connected from a wellhead to a drilling ship over a vertical distance of hundreds or thousands of feet, even a small movement of the drilling ship relative to the wellhead can cause enormous bending in the tubular.

Facilities and test beds for testing land based equipment does not produce the stresses seen offshore. The loads seen in subsea oilfield equipment are often several times to several orders of magnitude higher than land operations. As a result, testing and verifying the strength of the equipment is more difficult.

Load frames suitable for subsea oilfield equipment testing are large and expensive. Conventional frame designs are often configured to apply primary tension loadings. These frame designs typically include two or more structural members in parallel to the test sample. The two or more structural members are connected to platen ends. The test sample is then loaded typically by one or more hydraulic cylinders.

These hydraulic cylinders apply a tension force to the sample, however other loads can be applied as well. For instance, a bending load can be applied by a hydraulic cylinder loading from the side. Combined tension and bending loading can also be applied. The problem with the typical design is that the tension and bending loads must be contained within the test structure itself. The test structure must be sufficiently strong such that it too does not deform significantly in response to the loads applied to the test sample. As a result, simply increasing the test load capacity of a test structure using more powerful cylinders can cause the test structure to become too large and too expensive.

An example of current designs includes a sample test article, such as a tubular, bolted perpendicular to two beams to form a "H pattern" setup. Two hydraulic cylinders are connected to both beams and lined up parallel with the sample test article. The hydraulic cylinders can be pressurized the same amount to apply an axial load, or they can apply different forces to induce a moment in the test article. To test ever larger loads however requires larger hydraulic cylinders, driving up the costs. Moreover, in this setup the test article is in part supporting the test structure because the hydraulic cylinders are typically connected to the beams via pins. This allows unwanted forces in the test article during testing.

Furthermore, hydraulic cylinders are precision devices that also increase exponentially in cost as the size increases. There is a point where the cylinders themselves become too large and too expensive to test samples beyond a certain point. As a result, there exists a need to develop a test bed for subsea equipment that does not rely on ever increasing test structures and hydraulic cylinders.

SUMMARY OF EXAMPLES OF THE INVENTION

There currently exists a need to provide test structures that can test oilfield equipment at higher magnitudes than are currently practical. The test structure needs to be able to maintain rigidity and not rely on the test article itself for support. More importantly, the test structure needs to rely on existing hydraulic cylinders.

An example of an embodiment of the present invention includes a load frame test device comprising a frame, a support column, a first lever rotatable about a first pivot pin and attached to a first hydraulic cylinder about a second pivot pin at a first end, a second lever rotatable about the first pivot pin and attached to a second hydraulic cylinder about a third pivot pin at a first end, a first test article interface coupled to the second lever, and a second test article interface rotatable about a second pivot pin.

A variation of the embodiment may further comprise a second test article interface coupled to a lever rotatable about a pin with the frame, wherein the lever is connected to the second hydraulic cylinder at a first end. The first force may apply a substantially axial load. The second force may apply a substantially bending moment. The first force may apply a substantially axial load on the test article and the second force may apply a bending moment. The first hydraulic cylinder is further coupled to the frame. The first lever may be further attached to the frame about a fourth pivot pin at a second end. The first test article interface may be a split clamp. The second test article interface may be a split clamp. The embodiment may further comprise a tubular test article, a flange test article, or a welded connection test article, threaded connection test article.

Another example of an embodiment of the present invention may include a load frame test system comprising a frame, a support column, a test article, a first lever rotatable about a first pivot pin and attached to a first means for actuation about a second pivot pin at a first end, wherein the first hydraulic cylinder generates a first force, a second lever rotatable about the first pivot pin and attached to a second means for actuation about a third pivot pin at a first end, wherein the second hydraulic cylinder generates a second force, the test article interface coupled to the second lever at a first end and coupled to the frame at a second end, and a second test article interface rotatable about a second pivot pin, wherein the first force applies a substantially tensile load in the test article interface and the second force applies a bending moment in the test article.

A variation of the embodiment may further comprise a second test article interface coupled to a lever rotatable about a pin with the frame. Another variation may have a lever connected to the second means for actuation at a first end. The first means for actuation is may be coupled to the frame. The first lever may further be attached to the frame about a fourth pivot pin at a second end. The first test article interface may be a split clamp. The second test article interface may be a split clamp. The test article may be a tubular. The first means for actuation may be a hydraulic actuator. The second means for actuation may be a hydraulic actuator. The first test article interface may a bolted flange. The first test article interface may be an end cap welded to a bar. The first test article interface may be a welded end cap.

Another example of an embodiment of the present invention may include a method for testing an article comprising a means for coupling the first end of the tubular, a means for coupling the second end of the tubular, a means for applying a first force, a means for applying a second force, a means for converting the first force into a third force, a means for converting the second force into a fourth force, a means for converting the third force into a tensile stress in the tubular, and a means for converting the fourth force into a bending moment in the tubular.

A variation of the embodiment may include the means for coupling the first end of the tubular using a split clamp. The means for coupling the second end of the tubular may be a split clamp. The means for applying a first force may comprise pressurizing a first hydraulic fluid. The means for applying a second force may comprise pressurizing a second hydraulic fluid. The means for converting the first force into a third force may include a first lever. The means for converting the second force into a fourth force may include a second lever. The means for converting the third force into a tensile stress may include rotating the third force. The means for converting the fourth force into a bending moment may include applying the fourth force a distance away from the test article.

Another example of an embodiment may include a lever frame assembly comprising a support, a crosshead, rigidly connected with said support at a first location on said support, an upper outside lever, pivotally connected to said support at a second location on said support, an outer hydraulic cylinder connected between said upper outside lever at an upper outside lever arm pivot and said crosshead at a crosshead outside lever arm pivot, an inner hydraulic cylinder connected between an upper inner lever at an upper inner lever arm pivot and a lower inner lever at a lower inner lever arm pivot of said crosshead, an upper lever connection pivotally connecting said upper outside lever with said upper inner lever; and a lower lever connection pivotally connecting said lower inside lever with said crosshead.

A variation of the embodiment may further comprising an upper test article connection located on said upper inner lever and a lower test article connection located on said lower inner lever. The variation may have said upper and said lower test article connections comprising split clamps position to connect said upper test article connection with a test article and said lower test article connection with a test article. Another variation may include upper test article connection being included at least partly within an arm of said upper inner lever.

Another example of an embodiment may include a method of applying a bending moment to a test article, the method comprising applying a bending moment to the test article, wherein a compression force is applied to the test article, and applying an axial load to the text article, wherein said axial load at least partially counters the compression force.

A variation of the embodiment may further include applying a variety of stress combinations in the test article through said applying a bending moment and an axial load. Furthermore, applying an axial load fully compensates for any stresses other than a bending moment caused by said applying a bending moment.

Another example of an embodiment may include a system of applying a bending moment to a test article, the system comprising a means for applying a bending moment to the test article, wherein a compression force is applied to the test article, and a means for applying an axial load to the text article, wherein said axial load at least partially counters the compression force.

A variation of the example embodiment may include the means for applying a bending moment and said means for applying an axial load applying a variety of stress combinations in the test article. Another variation may include said means for applying an axial load fully compensating for any stresses other than a bending moment caused by said applying a bending moment. Another variation may include said means for applying a bending moment comprising a hydraulic cylinder pivotally connected between a crosshead and a pivotal connection with an upper outer lever arm of an upper lever, wherein the upper outer lever arm is pivotally connected to a support, wherein said support is rigidly connected to the crosshead, and wherein test piece connections are located on the upper lever and the crosshead. Another variation of the embodiment may include said means for applying an axial load comprising a hydraulic cylinder pivotally connected between the crosshead and a pivotal connection with the upper lever.

BRIEF DESCRIPTION OF THE DRAWINGS

For a thorough understating of the present invention, reference is made to the following detailed description of the preferred embodiments, taken in conjunction with the accompanying drawings in which reference numbers designate like or similar elements throughout the several figures. Briefly.

DETAILED DESCRIPTION OF EXAMPLES OF THE INVENTION

In the following description, certain terms have been used for brevity, clarity, and examples. No unnecessary limitations are implied and such terms are used for descriptive purposes only and are intended to be broadly construed. The different apparatus and method steps described herein may be used alone or in combination with other systems and method steps. It is to be expected that various equivalents, alternatives, and modifications are possible within the scope of the appended claims.

Figure 1:
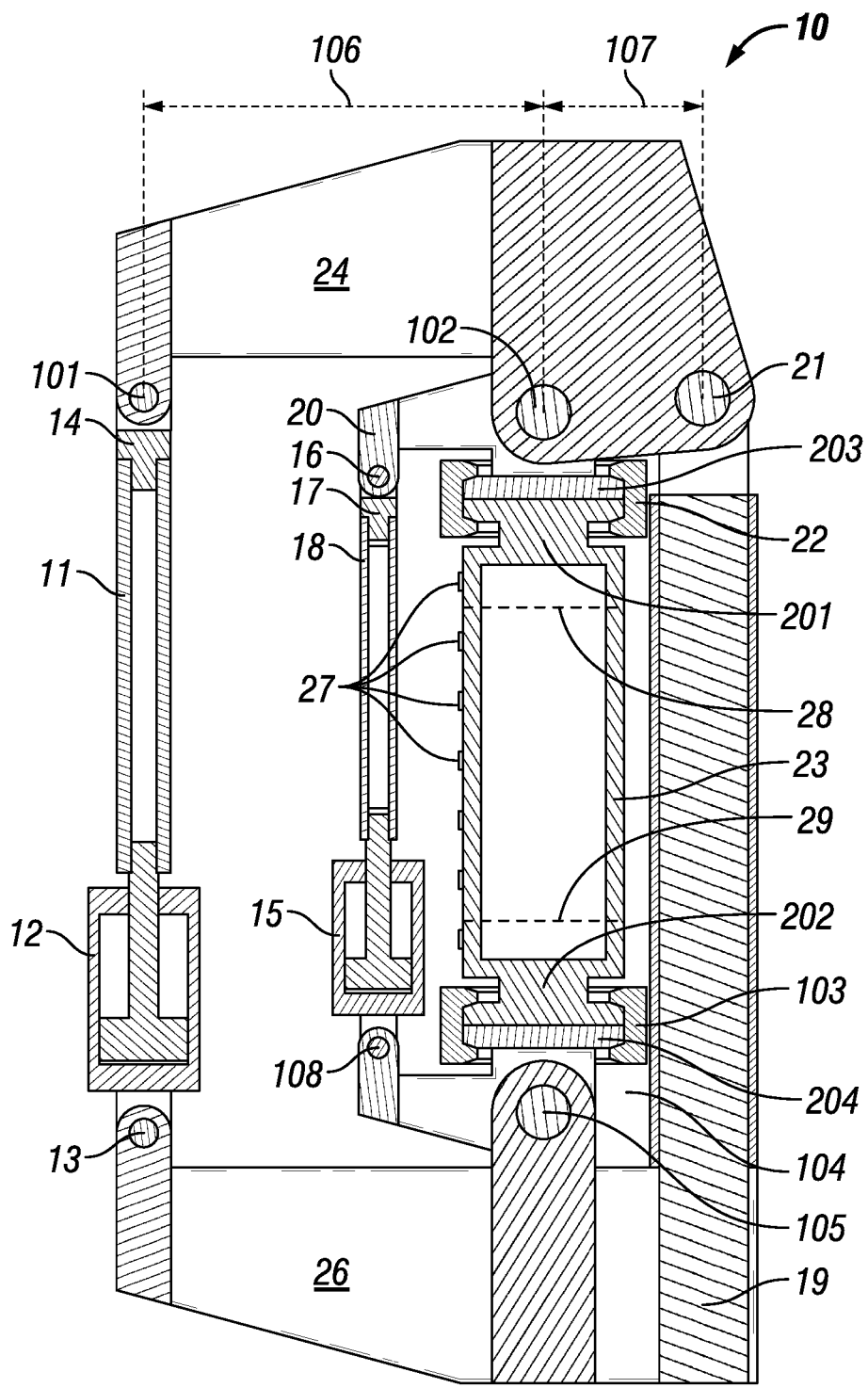
FIG. 1 is an example of an embodiment of the load frame test assembly.

An example of the invention is illustrated in FIG. 1. An example of a lever frame assembly 10 configured for a high variety of bending and tension combinations is shown. The frame assembly 10 uses two hydraulic cylinders, a hydraulic cylinder 12 and hydraulic cylinder 15. The hydraulic cylinder 12 is connected to the lower lever 26 via an axial pin 13. The hydraulic cylinder 12 is further connected to an extension member 11, which is then connected to axial yoke 14. Axial yoke 14 connects to the upper lever 24 via axial pin 101.

The upper lever 24 connects to the column 19 via pin 21. Column 19 is welded to lower lever 26. The upper lever 24 also connects to the test article 23 via pin 102. Pin 102 connects the lever 24 to the upper lever arm 20. Lever arm 20 is further connected to the bending yoke 17 using bending pin 16. Bending yoke 17 transmits forces from the hydraulic cylinder 15 to the upper lever arm 20. Hydraulic cylinder 15 is connected to support column 19 at pin 105 via the lower lever arm 104.

The test article 23 is connected to the upper lever arm 20 using split clamp 22. The test article 23 is further connected to the lower lever arm 104 using split clamp 103. In this example the split clamp 22 and 103 allows for easier alignment of the test article 23. Strain gauges 27 can be located at one or more locations on the test article 23 to gather measurements. The test article 23 in this example is a tubular that is welded (weld beads 28 and 29) to end caps 201 and 202. Other types of test articles could include flanges, welded connections, threaded connections, or any other components used in the industry. The split clamp 22 and 103 could be of a threaded design. In the threaded split clamp the split clamp may have two halves that bolt together. Each halve will have internal threads. The end caps 201 and 202 may have matching external threads along with connections 203 and 204. The split clamp 22 can then bolt together over connection 203 and end cap 201 and the mated threads will lock all three components together. The same mated thread connection is possible for split clamp 103, end cap 202, and connection 204. The thread types may include unified, metric, square, ACME, Buttress, or other known thread types.

As the hydraulic cylinder 12 can apply an axial force to the test article 23. The force applied results in tensile stresses in the test article 23. The force supplied by the hydraulic cylinder 12 is multiplied due to the leverage afforded by lever 24. As can be seen, the distance 106 between pin 101 and 102 causes the forces seen by the test article 23 to be several times higher than the force applied at hydraulic cylinder 12.

Hydraulic cylinder 15 can apply a bending moment onto the test article 23. The upper lever arm 20 and lower lever arm 104 apply a bending moment to the test article 23. Hydraulic cylinder 15 may be used in combination with hydraulic cylinder 12 to generate a variety of stress combinations in the test article 23.

Hydraulic cylinder 12 can apply an axial load to the test article 23. Hydraulic cylinder 12 can also be used to counter compression forces caused by bending hydraulic cylinder 15. Therefore, a combination of hydraulic cylinder 12 and hydraulic cylinder 15 can be used to create a pure bending moment in test article 23.

Hydraulic cylinder 15 may transmit a bending force to test article 23. The hydraulic cylinder applies a force to the upper lever arm 20 and is fixed to the test specimen via split clamp 22, allowing the transmission of bending forces to the test article 23 as the lever arm 20 rotates about pin 102. Hydraulic cylinder 15 is connected to lower lever arm 104 using pin 108. This setup may subject the test article 23 to tensile and bending loads either separately or in combination.

Figure 2:
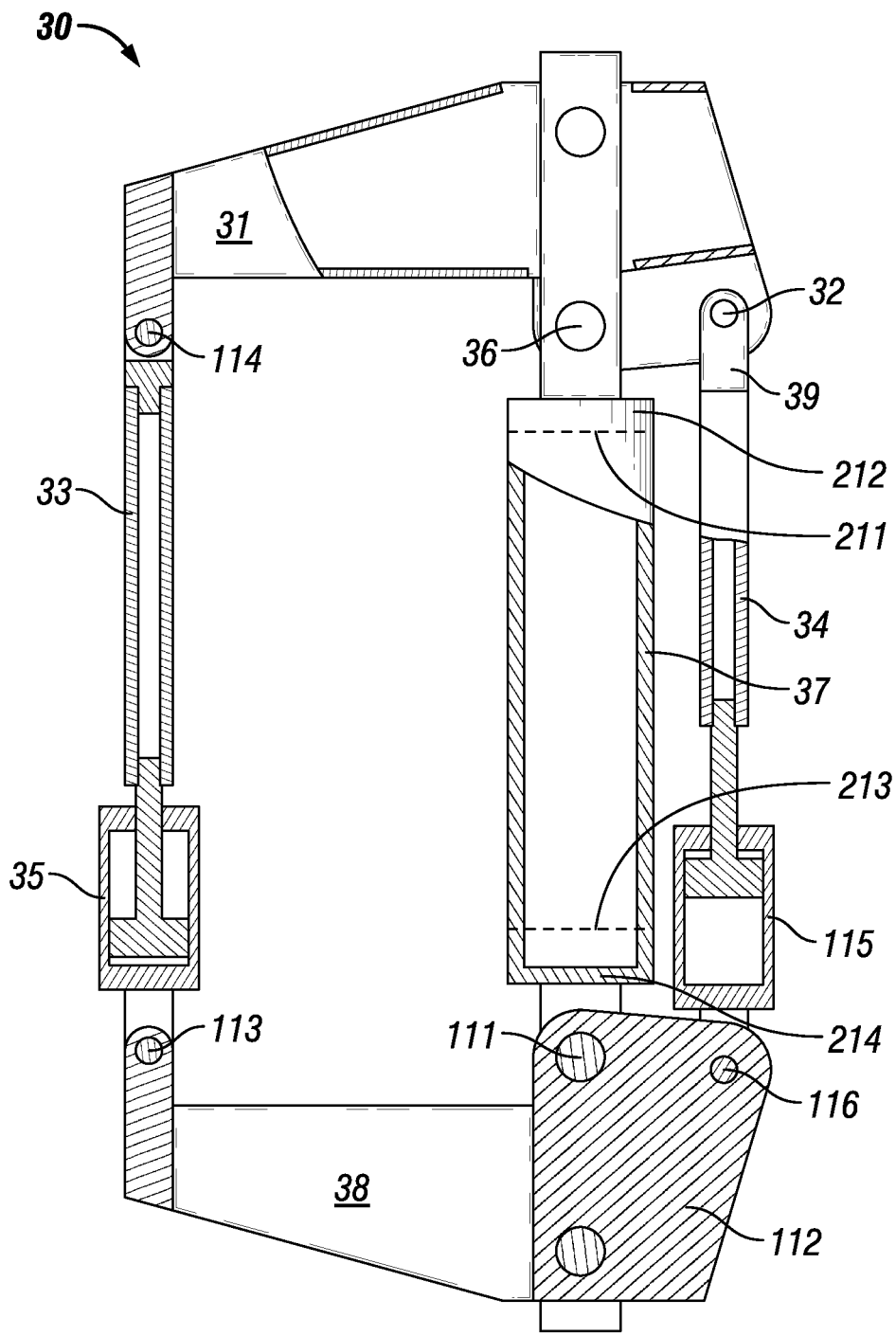
FIG. 2 is an example of an embodiment of the load frame test assembly.

Another configuration of the lever frame assembly 30 is shown in FIG. 2. This configuration allows for higher moments or pure bending. The test article 37 is connected to the upper lever 31 at pin 36 and to the lower crosshead 112 at pin 111. A hydraulic cylinder 35 is connected to the lower lever 38 at pin 113. The hydraulic cylinder 35 connects to extension member 33, which is then connected to the upper lever 31 via pin 114. A second hydraulic cylinder 115 is connected to the lower crosshead 112 via pin 116. The second hydraulic cylinder 115 is further connected to the extension member 34 and further to the upper lever 31 via yoke 39 and pin 32. In this example the test article 37 is welded (shown by weld beads 211 and 213) to upper end cap 212 and lower end cap 214.

Hydraulic cylinder 35 can apply a tensile load to test article 37. This tensile loading is leveraged by upper lever 31. The second hydraulic cylinder 115 applies a bending moment to the test article 37. This configuration allows for testing test article 37 under tensile loading, bending, or a combination of tension and bending.

Figure 3:
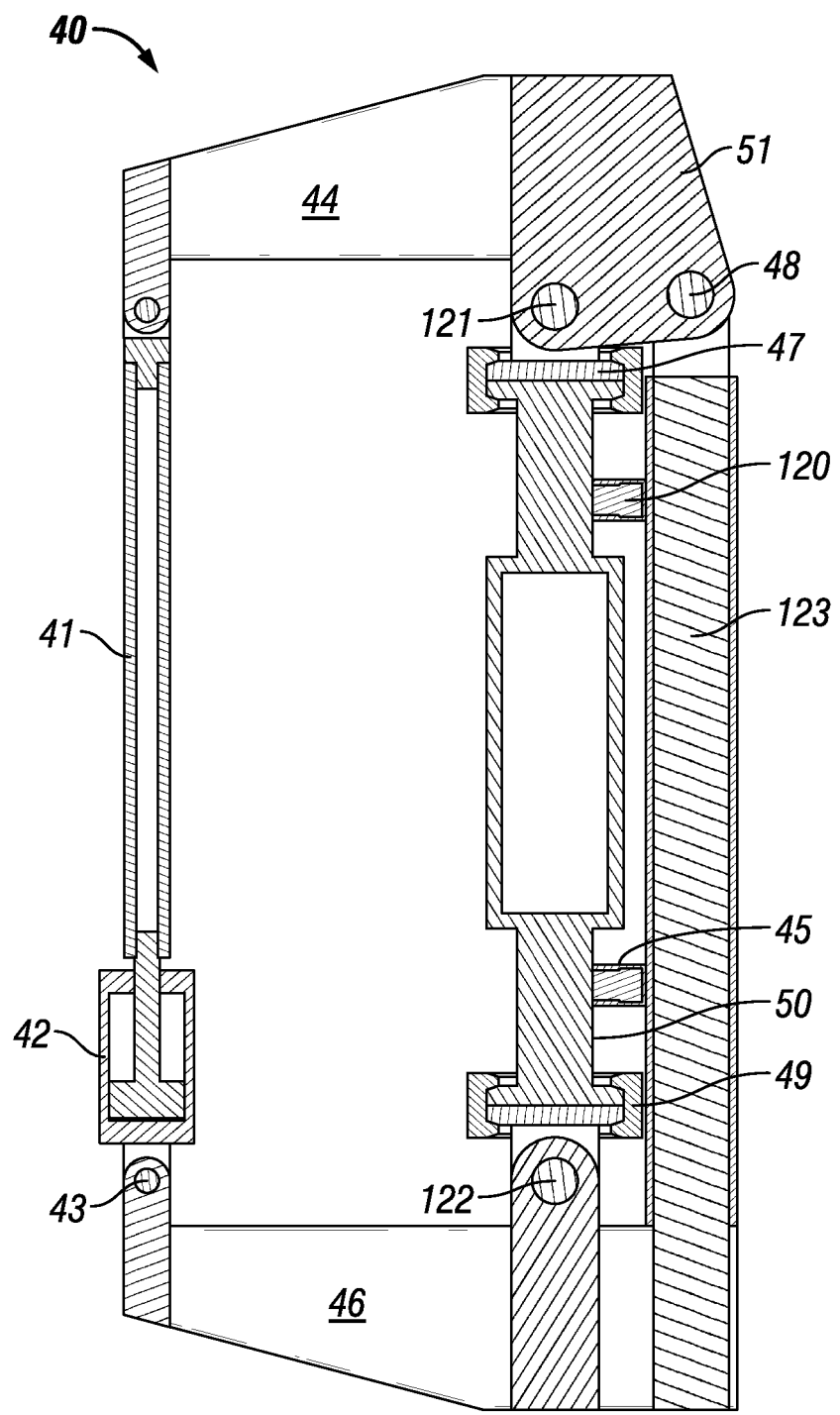
FIG. 3 is an example of an embodiment of the load frame test assembly.

Another configuration of the lever frame assembly 40 is shown in FIG. 3. Under this configuration tension is applied to the test article 50 by a leveraged hydraulic cylinder 42. Bending forces are applied by rams 45 and 120. The test article 50 is held in place by split clamps 47 and 49. The test article 50 is connected to the upper crosshead 51 via pin 121. The test article 50 is connected to the lower lever 46 via pin 122. The hydraulic cylinder 42 is connected to the lower lever 46 via pin 43. The hydraulic cylinder 42 is connected to the upper crosshead 51 via extension member 41 and pin 44. Upper crosshead 51 is connected to the side member 123 via pin 48. Support column 123 may be welded or fixed in a fashion known in the art to lower lever 46.

The configuration shown in FIG. 3 applies a leveraged axial from lower hydraulic cylinder 42 to the test article 50. A bending moment may be applied to the test article 50 by rams 120 and 45.

Figure 4:
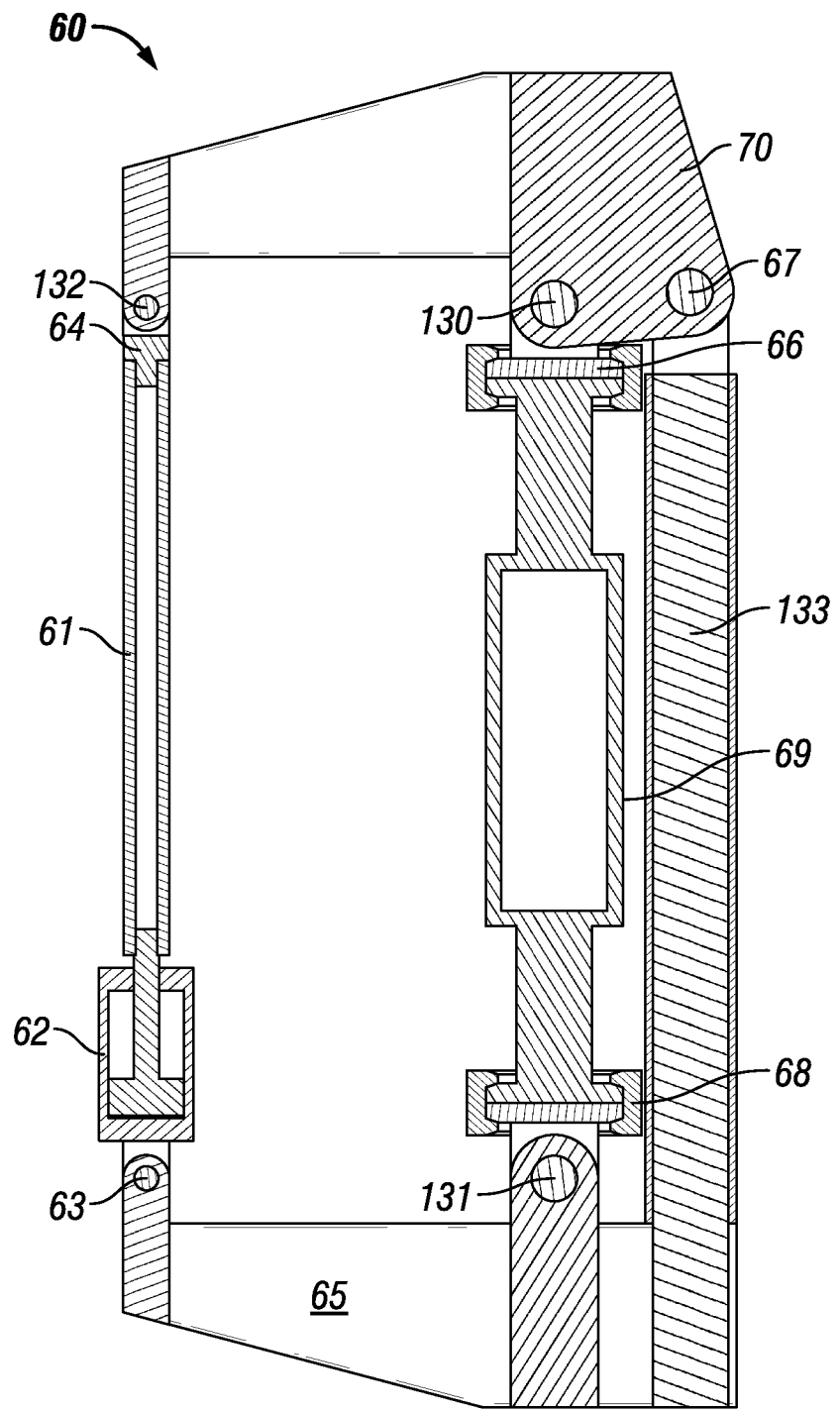
FIG. 4 is an example of an embodiment of the load frame test assembly.

Another configuration of the lever frame assembly 60 is shown in FIG. 4. This configuration is design to subject a test article 69 to pure tension using leveraged force from hydraulic cylinder 62. Test article 69 is coupled to the lever frame assembly 60 using two couples secured with split clamps 66 and 68. The upper split clamp 66 connects the test article 69 to upper crosshead 70 via pin 130. The lower split clamp 68 connects the test article 69 to lower lever 65 via pin 131. Force is applied by hydraulic cylinder 62. Hydraulic cylinder 62 is connected to the lower lever 65 via pin 63. Hydraulic cylinder 62 is further connected to upper crosshead 70 via extension member 61 connecting to yoke 64 and then to pin 132. Side member 133 connects via pin 67 to upper crosshead 70. Side member 133 is attached to lower lever 65.

In the configuration of FIG. 4, a force is applied to the test article 69 using the hydraulic cylinder 62. The offset of hydraulic cylinder 62 from test article 69 allows leverage to multiply the force seen at the test article 69. Hydraulic cylinder 62 is connected to member 61, which connects to yoke 64 and is pinned to upper crosshead 70 at pin 132. Hydraulic cylinder is also connected to lower crosshead 65 via pin 63. Upper crosshead 70 connects to support column 133 at pin 67. Upper connector 66 is pinned to upper crosshead 70 at pin 130 and is further clamped to test article 69. The test article 69 is further coupled to the lower crosshead 65 using split clamp 68 and pin 131. Further, because the test article is pinned at both ends, movement of the upper crosshead 70 or lower lever 65 is compensated for, leaving the test article 69 subjected to substantially pure tensile forces.

Figure 5:
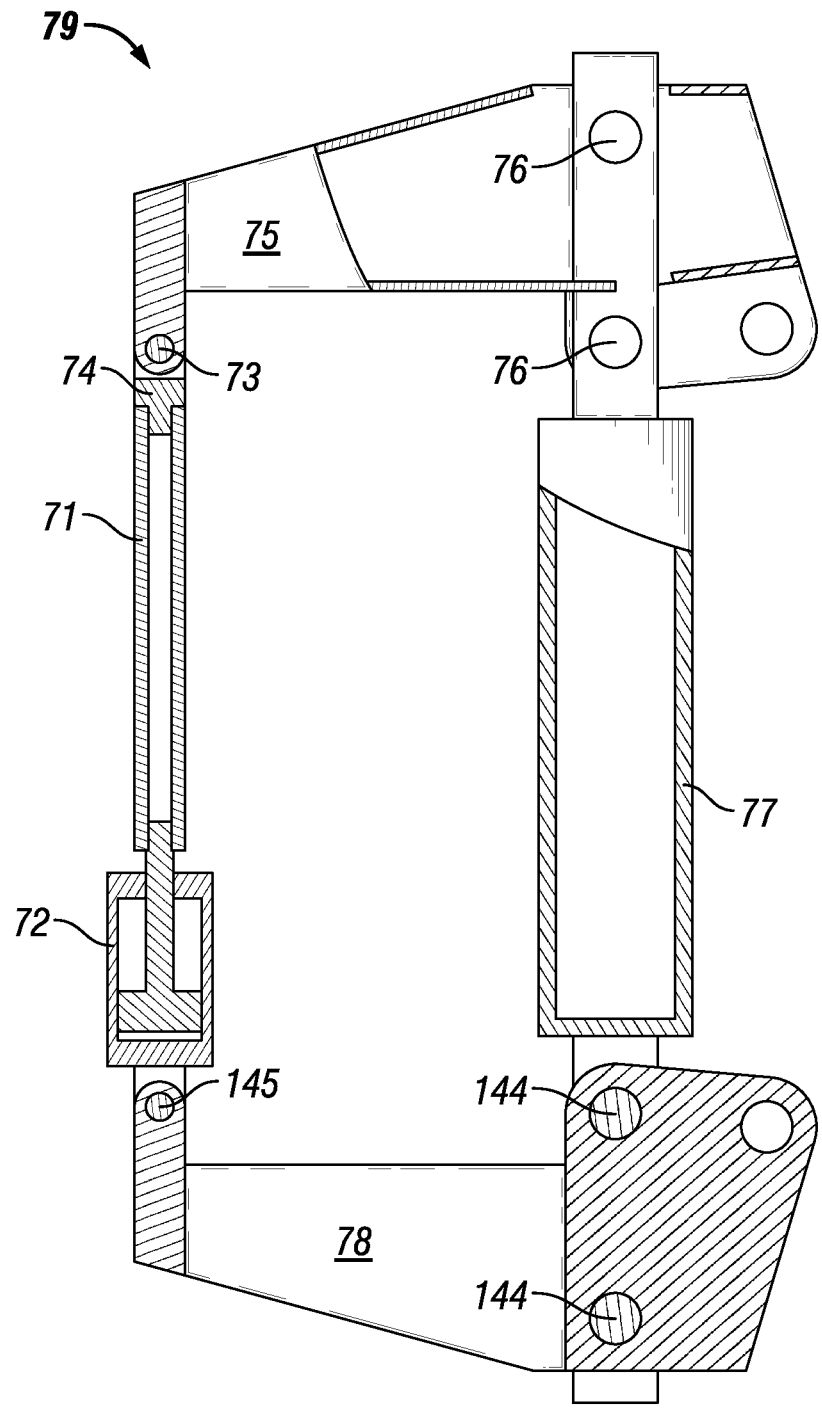
FIG. 5 is an example of an embodiment of the load frame test assembly.

Another example of a possible configuration for lever frame assembly 79 is shown in FIG. 5. In this example, the lever frame assembly 79 is configured to apply a high moment without tension control. Test article 77 is fixed to upper lever 75 via pins 76. The test article 77 is also connected to lower lever 78 via pin 144. The lower lever 78 is connected to the bottom of hydraulic cylinder 72 via pin 145. Hydraulic cylinder 72 is connected to extension member 71. Extension member 71 is connected to yoke 74 that is also connected to the upper lever 75 via pin 73.

Figure 6:
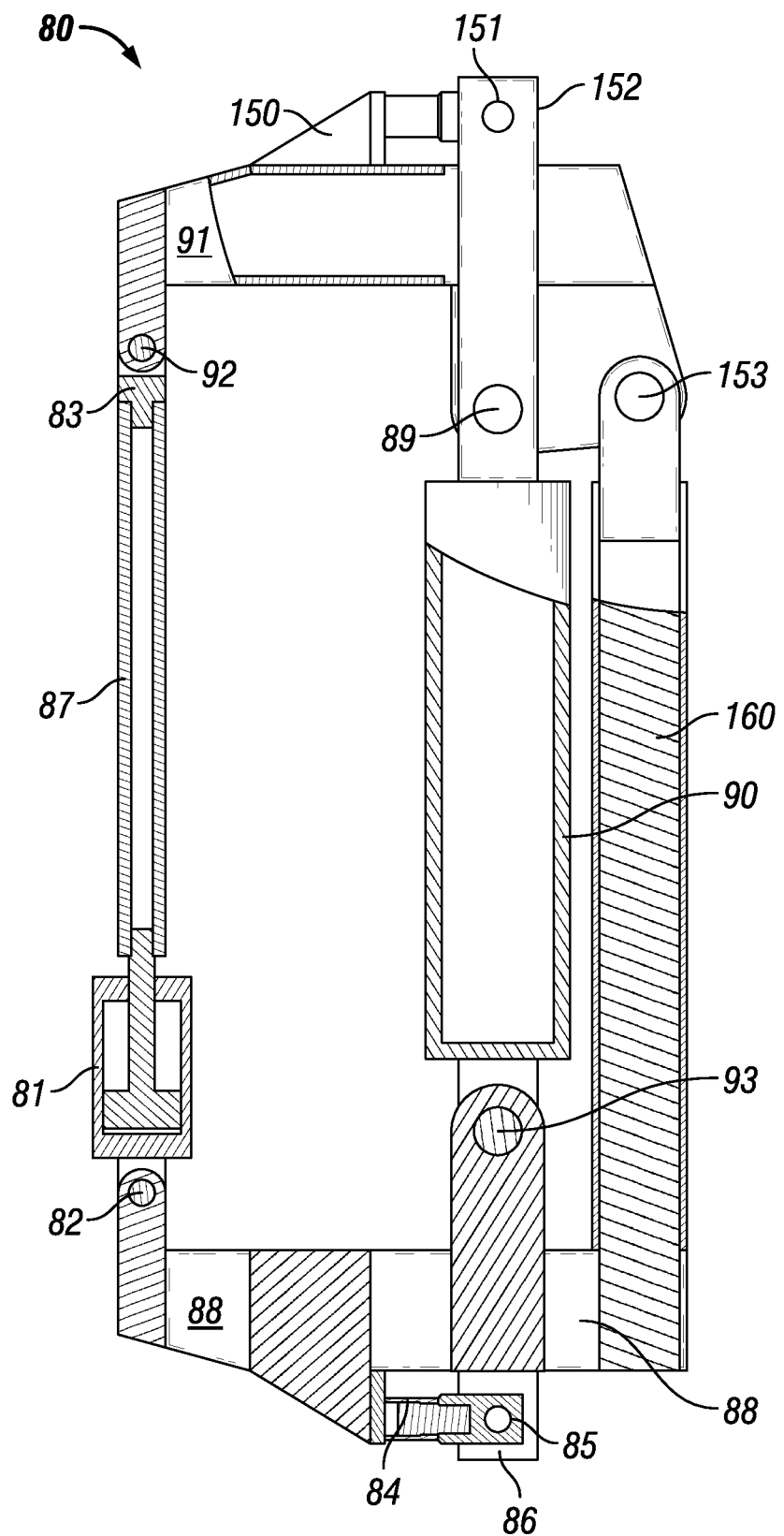
FIG. 6 is an example of an embodiment of the load frame test assembly.

Another example of a configuration for lever frame assembly 80 is shown in FIG. 6. In this example, the lever frame assembly 80 puts the test article 90 into tension by leveraging force from hydraulic cylinder 81. In addition, either or both hydraulic cylinder 150 and 84 may apply a bending moment to test article 90. Hydraulic cylinders 150 and 84 may individually or simultaneously put desired bending loads on test article 90. Hydraulic cylinder 81 is connected to the lower crosshead 88 using pin 82. Hydraulic cylinder 81 is connected to extension member 87. Extension member 87 has an axial yoke 83 at one end that is connected to the upper lever 91 using pin 92. Upper lever 91 is connected to test article 90 using pin 89. Upper lever 91 is connected to support column 160 at pin 153. Test article 90 is connected to the lower crosshead 88 using pin 93. Test article 90 has an upper tang 152 and a lower tang 86. A hydraulic cylinder 84 is mounted onto lower crosshead 88 and is configured to apply a side force against lower tang 86 using pin 85. A hydraulic cylinder 150 is mounted onto the upper lever 91 and is configured to apply a side force to tang 152 via pin 151. Either of the three hydraulic cylinders 81, 84, or 150 may be used either together or separately to apply the desired combinations of bending and tensile loading to the test article 90.

Figure 7:
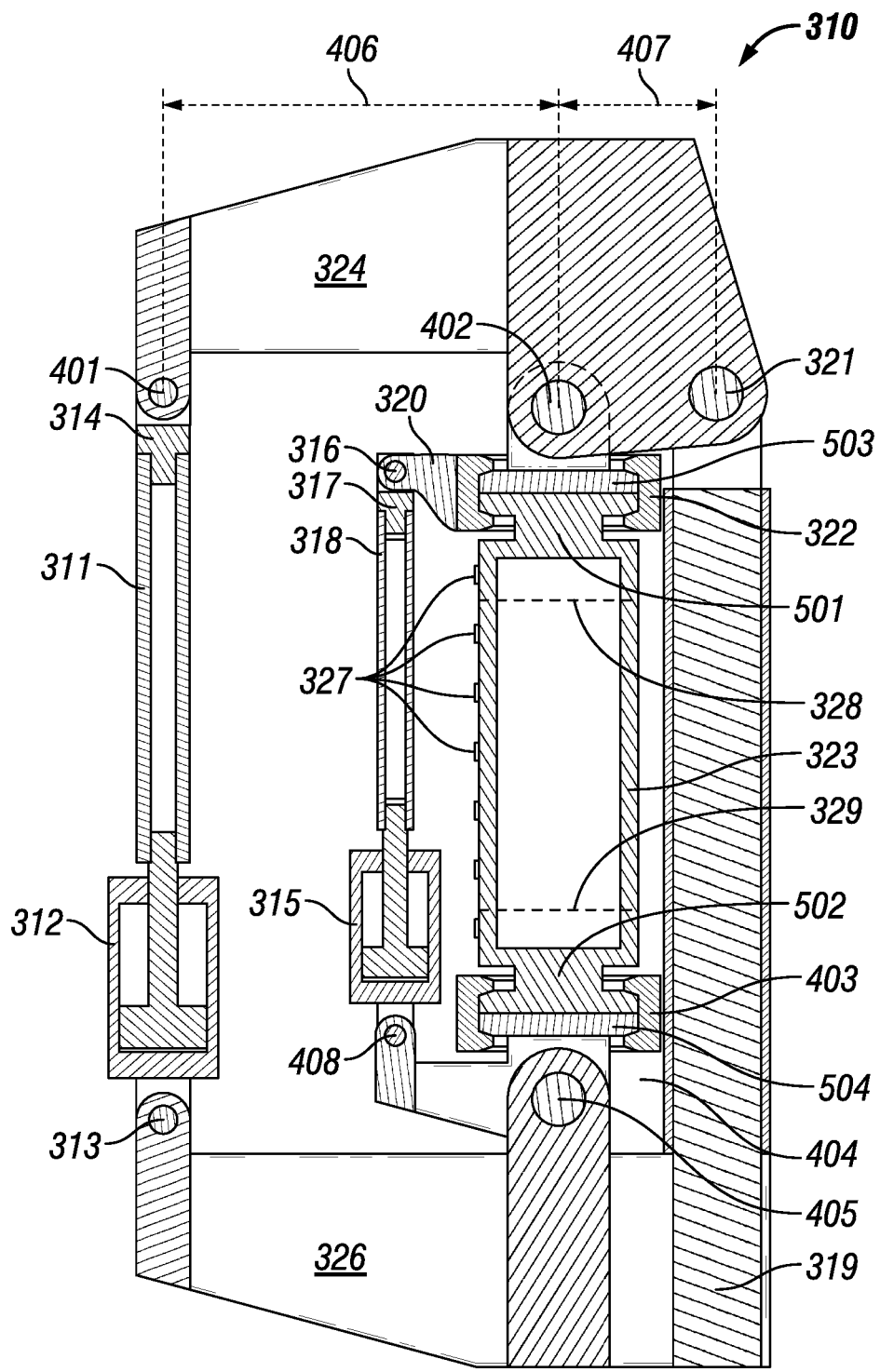
FIG. 7 is an example of an embodiment of the load frame test assembly.

An example of the invention is illustrated in FIG. 7. An example of a lever frame assembly 310 configured for a high variety of bending and tension combinations is shown. The frame assembly 310 uses two hydraulic cylinders, a hydraulic cylinder 312 and hydraulic cylinder 315. The hydraulic cylinder 312 is connected to the lower lever 326 via an axial pin 313. The hydraulic cylinder 312 is further connected to an extension member 311, which is then connected to axial yoke 314. Axial yoke 314 connects to the upper lever 324 via axial pin 401.

Upper lever 324 connects to the column 319 via pin 321. Column 319 is welded to lower lever 326. Upper lever 324 also connects to the test article 323 via pin 402. Pin 402 connects upper lever 324 to the upper lever arm 320. Upper lever arm 320 is further connected to the bending yoke 317 using bending pin 316. Bending yoke 317 transmits forces from the hydraulic cylinder 315 to the upper lever arm 320. Hydraulic cylinder 315 is connected to column 319 at pin 405 via the lower lever arm 404.

The test article 323 is connected to the upper lever arm 320 using split clamp 322. The test article 323 is further connected to the lower lever arm 404 using split clamp 403. In this example the split clamp 322 and 403 allows for easier alignment of the test article 323. Strain gauges 327 can be located at one or more locations on the test article 323 to gather measurements. The test article 323 in this example is a tubular that is welded (weld beads 328 and 329) to end caps 501 and 502. Other types of test articles could include flanges, welded connections, threaded connections, or any other components used in the industry. The split clamp 322 and 403 could be of a threaded design. In the threaded split clamp the split clamp will have two halves that bolt together. Each halve will have internal threads. The end caps 501 and 502 may have matching external threads along with connections 503 and 504. The split clamp 322 can then bolt together over connection 503 and end cap 501 and the mated threads will lock all three components together. The same mated thread connection is possible for split clamp 403, end cap 502, and connection 504. The thread types may include unified, metric, square, ACME, Buttress, or other known thread types.

As the hydraulic cylinder 312 can apply an axial force to the test article 323. The force applied results in tensile stresses in the test article 323. The force supplied by the hydraulic cylinder 312 is multiplied due to the leverage afforded by upper lever 324. As can be seen, the distance 406 between pin 401 and 402 causes the forces seen by the test article 323 to be several higher times than the forces applied at the hydraulic cylinder 312.

Hydraulic cylinder 315 can apply a bending moment onto the test article 323. The upper lever arm 320 and lower lever arm 404 apply a bending moment to the test article. Hydraulic cylinder 315 may be used in combination with hydraulic cylinder 312 to generate a variety of stress combinations in the test article 323.

Hydraulic cylinder 312 can apply an axial load to the test article 323. Hydraulic cylinder 312 can also be used to counter compression forces caused by hydraulic cylinder 315. Therefore, a combination of hydraulic cylinder 312 and hydraulic cylinder 315 can be used to create a pure bending moment in test article 323.

Hydraulic cylinder 315 does transmit a bending force to the test article when pressurized. The hydraulic cylinder applies a force to the upper lever arm 320 and is fixed to the test specimen via split clamp 322, allowing the transmission of bending forces to the test article 323 as the lever arm 320 rotates about pin 402. This setup may subject the test article 323 to tensile and bending loads either separately or in combination. Hydraulic cylinder 315 is coupled to lower lever arm 404 via pin 408.

Although the invention has been described in terms of particular embodiments which are set forth in detail, it should be understood that this is by illustration only and that the invention is not necessarily limited thereto. Alternative embodiments and operating techniques will become apparent to those of ordinary skill in the art in view of the present disclosure. Accordingly, modifications of the invention are contemplated which may be made without departing from the spirit of the claimed invention.

What is claimed is:
1. A load frame test device comprising:
   a support column;
   a first crosshead;
   a first lever rotatable about a first pivot pin and attached to a first hydraulic cylinder about a second pivot pin at a first end;
   a second lever rotatable about the first pivot pin and attached to a second hydraulic cylinder about a third pivot pin at a first end;
   a first test article interface coupled to the second lever; and
   a second test article interface rotatable about a second pivot pin.
2. The apparatus of claim 1, further comprising a second test article interface coupled to a lever rotatable about a pin with the frame.

3. The apparatus of claim 2, wherein the lever is connected to the second hydraulic cylinder at a first end.

4. The apparatus of claim 1, wherein the first force applies a substantially axial load.

5. The apparatus of claim 1, wherein the second force applies a substantially bending moment.

6. The apparatus of claim 1, wherein the first force applies a substantially axial load in the test article and the second force applies a bending moment.

7. The apparatus of claim 1, wherein the first hydraulic cylinder is coupled to the frame.

8. The apparatus of claim 1, wherein the first lever is further attached to the frame about a fourth pivot pin at a second end.

9. The apparatus of claim 1, wherein the first test article interface is a split clamp.

10. The apparatus of claim 1, where n the second test article interface is a split clamp.

11. The apparatus of claim 1, further comprising a tubular test article.

12. The apparatus of claim 1, further comprising a flange test article.

13. The apparatus of claim 1, further comprising a connection test article.

14. The apparatus of claim 1, further comprising a welded test article.

15. A load frame test system comprising:
a frame;
a test article;
a first lever rotatable about a first pivot pin and attached to a first means for actuation about a second pivot pin at a first end, wherein the first hydraulic, cylinder generates a first force;
a second lever rotatable about the first pivot pin and attached to a second means for actuation about a third pivot pin at a first end, wherein the second hydraulic cylinder generates a second force;
the test article interface coupled to the second lever at a first end and coupled to the frame at a second end; and
a second test article interface rotatable about a second pivot pin, wherein the first force applies a substantially axial load in the test article interface and the second force applies a bending moment in the test article.

16. The apparatus of claim 15, further comprising a second test article interface coupled to a lever rotatable about a pin with the frame.

17. The apparatus of claim 16, wherein the lever is connected to the second means for actuation at a first end.

18. The apparatus of claim 15, wherein the first means for actuation is coupled to the frame.

19. The apparatus of claim 15, wherein the first lever is further attached to the frame about a fourth pivot pin at a second end.

20. The apparatus of claim 15, wherein the first test article interface is a split clamp.

21. The apparatus of claim 15, wherein the second test article interface is a split clamp.

22. The apparatus of claim 15, wherein the test article is a tubular.

23. The apparatus of claim 15, wherein the first means for actuation is a hydraulic actuator.

24. The apparatus of claim 15, wherein the second means for actuation is a hydraulic actuator.

25. The apparatus of claim 15, wherein the first test article interface is a bolted flange.

26. The apparatus of claim 15, wherein the first test article interface is a custom welded bar.

27. The apparatus of claim 15, wherein the first test article interface is a welded end cap.

28. A lever frame assembly comprising:
a support,
a crosshead, rigidly connected with said support at a first location on, said support;
an upper outside lever, pivotally connected to said support at a second location on said support;
an outer hydraulic cylinder connected between
said upper outside lever at an upper outside lever arm pivot and
said crosshead at a crosshead outside lever arm pivot;
an inner hydraulic cylinder connected between
an upper inner lever at an upper inner lever an pivot and
a lower inner lever at a lower inner lever arm pivot of said crosshead;
an upper lever connection pivotally connecting said upper outside lever with said upper inner lever; and
a lower lever connection pivotally connecting said lower inside lever with said crosshead.

29. A frame as in claim 28 further comprising:
an upper test article connection located on said upper inner lever and
a lower test article connection located on said lower inner lever.

30. A frame as in claim 29 wherein said upper and said lower test article connections comprise split clamps position to connect said upper test article connection with a test article and said lower test article connection with a test article.

31. A frame as in claim 29 wherein said upper test article connection is included at least partly within an arm of said upper inner lever.

* * * * *